United States Patent [19]

Tagnon

[11] Patent Number: 4,517,980

[45] Date of Patent: May 21, 1985

[54] OPHTHALMIC SURGICAL LASER APPARATUS

[75] Inventor: Luc Tagnon, Saint Mande, France

[73] Assignee: Essilor International Cie Generale d'Optique, Creteil, France

[21] Appl. No.: 429,962

[22] Filed: Sep. 30, 1982

[30] Foreign Application Priority Data

Oct. 2, 1981 [FR] France .................. 81 18612

[51] Int. Cl.³ .................. A61N 5/00; A61B 17/36
[52] U.S. Cl. .................. 128/395; 128/303.1
[58] Field of Search ............. 128/303.1, 395, 396–398; 219/121 L, 121 LU, 121 LV

[56] References Cited

U.S. PATENT DOCUMENTS

| | | | |
|---|---|---|---|
| 3,710,798 | 1/1973 | Bredemeir .................. | 128/303 |
| 3,851,974 | 12/1974 | Ravussin et al. .................. | 356/153 |
| 4,079,230 | 3/1978 | Mitauchi et al. .................. | 219/121 L |
| 4,099,141 | 7/1978 | Leblanc et al. .................. | 372/33 X |
| 4,289,378 | 9/1981 | Remy et al. .................. | 128/395 X |
| 4,309,998 | 1/1982 | Aron née Rosa et al. .................. | 128/395 X |
| 4,408,602 | 10/1983 | Nakajima .................. | 128/303.1 |
| 4,409,979 | 10/1983 | Roussel et al. .................. | 128/395 X |

FOREIGN PATENT DOCUMENTS

| | | |
|---|---|---|
| 0007256 | 1/1980 | European Pat. Off. . |
| 0030210 | 6/1981 | European Pat. Off. . |
| 156687 | 12/1980 | Japan .................. 219/121 LV |

OTHER PUBLICATIONS

Mutze, *ABC der Optic*, 1960, p. 26, col. 2, lines 4–6; Fig. 4.

*Primary Examiner*—Edward M. Coven
*Attorney, Agent, or Firm*—Charles A. Brown; Charles E. Brown

[57] ABSTRACT

An ophthalmic surgical apparatus is disclosed comprising a main laser generator for emitting an operating laser beam of infrared energy and an auxiliary laser generator for emitting a marker laser beam of visible light. The laser beams are superposed before reaching an operating system by a plurality of mirrors and a laser beam expander for each of the laser beams. The laser beam expanders have separate entrance lenses and a common exit lens. Preferably, the operating optical system comprises a focusing lens which doubles as the common exit lens of the laser beam expander.

12 Claims, 3 Drawing Figures

U.S. Patent    May 21, 1985    4,517,980
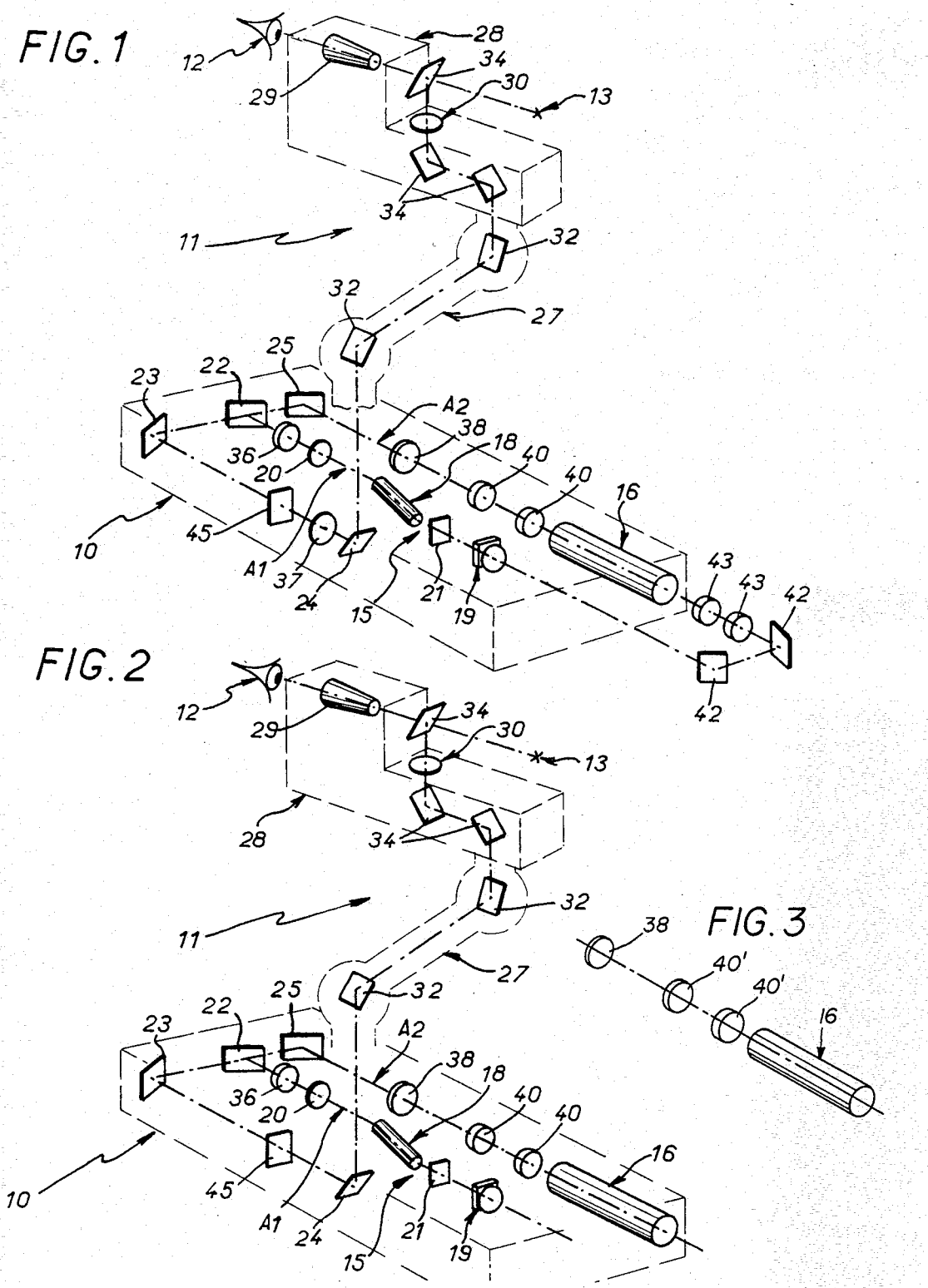

OPHTHALMIC SURGICAL LASER APPARATUS

FIELD OF THE INVENTION

The present invention relates generally to an ophthalmic surgical apparatus employing an operating laser generator for cutting tissues and a marker laser generator for aiming the operating laser generator.

Such surgical apparatus advantageously avoids scar tissue being formed after surgery.

The power of the light flux transported by the operating laser beam used must in practice be sufficiently high so that surgery is not performed by heat transfer but by optical breakdown, i.e., atomic dissociation of the tissues aimed at.

Besides the absence of heating there is a local formation of a plasma of sufficient density to be opaque to the radiation which produces it so that the tissues therebeyond, namely the retina, are advantageously protected from this radiation.

For the energy of the light flux carried by the operating beam to attain the sought-after high value, the pulses of the beam must be ultra short, of the order or at most several tenths of a picosecond. A YAG laser generator emitting infrared energy in the blocked mode is well adapted in this regard.

For the operator to see the marked or aimed-at spot of such an operating laser beam of infrared energy necessary for very precisely locating the operating site, it is common to associate with the main operating laser generator a low energy continuous marker laser generator of visible light.

An ophthalmic surgical laser apparatus comprising a main infrared energy laser generator and an auxiliary visible light laser generator is disclosed, in particular, in European patent publication No. 0007256 published Jan. 23, 1980.

In practice a series of mirrors are employed for superposing both laser beams at the entrance of an operating optical system essentially formed by a split lamp and comprising between the laser generator and the split lamp an articulated transfer arm for effecting the connection between these two components and a focusing lens for suitably concentrating the laser beams at the operating site. Each of the laser generators is associated with an optical device called a laser beam expander adapted to augment the diameter of the beam in order to reduce the surface density of light flux in the cross-sectional plane.

There is a triple reason for this. First of all, good location of the operating site must be obtained for a convergence of the laser beam of infrared energy as great as possible penetrating into the eye. Secondly, unnecessary transmutation must be avoided of tissues traversed upstream of the operating site and notably the epithelium of the cornea, by reducing the energy density in the section of the laser beam of infrared energy in these zones. Thirdly, damage to the conventional metal mirrors employed for superposing the two laser beams must be avoided.

Such a beam expander comprises at least an entrance lens and an exit lens. In the ophthalmic surgical laser apparatus disclosed in the above identified European patent publication the beam expanders employed which must be in part separate from each other owing to the need to handle the two laser beams separately, on account of their different wave lengths, are in fact entirely separate from each other.

Since the degree of beam expansion is of the order of ten, the focal length of the lenses must therefore be relatively short and consequently their focal power relatively high, of the order of 40 diopters for the entrance lens. The lenses have relatively small diameter openings which are particularly difficult to manufacture and to center.

OBJECT AND SUMMARY OF THE INVENTION

An object of the invention is to provide an ophthalmic surgical laser apparatus which enables the foregoing drawbacks to be overcome and which has additional advantages.

According to the invention there is provided an ophthalmic surgical laser generator comprising a main laser generator for emitting an operating laser beam of infrared energy and an auxiliary laser generator for emitting a marker laser beam of visible light, means for superposing the laser beams when they reach an entrance lens of an operating optical system, said means for superposing the laser beams including a plurality of mirrors, and a laser beam expander for each of the laser beams, said laser beam expanders having separate entrance lenses and a common exit lens.

Owing to this arrangement the common exit lens may be disposed as close as desired to the operating optical system and in any event remote from the entrance lenses of the beam expanders.

Thus, for a given expansion ratio the entrance and exit lenses may advantageously have relative long focal lengths and therefore relatively weak focal powers, e.g., of the order of 15 diopters for the entrance lenses. Such lenses may have greater manufacturing tolerances and admit of a more economical surfacing procedure. In addition they may also advantageously comply with larger locating tolerances.

The resulting construction of the laser surgical apparatus is therefore facilitated and the production cost is reduced. Its efficiency is nevertheless improved, since the laser beams have a smaller number of glass-air or air-glass interfaces to cross, which are sources of energy losses.

According to another feature of the invention the common exit lenses of the laser beam expanders also comprises the focusing lens of the operating lens system. The exit lens is therefore correspondingly more remote from the associated entrance lenses which contributes to the sought-after increase in the focal length of the entrance lenses.

Furthermore, the adjustments are made easier. Since the focusing lens of the operating lens system is disposed downstream of the transfer arm and the laser beams are therefore divergent in the transfer arm and not cylindrical, it is easier to permit their passage through the transfer arm, which is cylindrical, the only diaphragm encountered being the common exit lens of the beam expanders which has a converging function.

In the L a s a g AG European patent publication No. 0030210 a beam expander is associated with only the operating laser generator and comprises two lens, a first diverging lens and a second converging lens associated together. No beam expander is associated with the marker beam but rather an optical divider which comprises a prism which divides the beam into two subbeams. Moreover, the beam expander for the operating laser generator and the optical divder for the marker beam have no common component.

On the other hand in the alternative embodiment schematically illustrated in the aforesaid European patent publication there is a lens which is in common with the operating laser beam and the marker beam. But this lens is not the exit lens of the beam expander associated with the operating beam. On the contrary, the common lens is a focusing lens which may also be common to both the operating beam and the marker beam.

By contrast, in the present invention there is provided a beam expander for each of the operating beam and the marker beam, the beam expanders having a common exit lens.

The superposition of the operating laser beam and the marker laser beam according to the invention is effected at least in part inside the corresponding beam expanders along the common portion thereof by correspondingly adjusting the position of reflective mirrors interposed along the marker laser beam.

Preferably, according to the invention, the superposition of the operating and marker laser beams is obtained very simply by interposing along the marker laser beam two successive diasporameters, or even two ordinary lenses each of which induces a prism when the lens is eccentric, each of the lenses being movably mounted in its plane.

In either arrangement the reflective mirrors may advantageously be stationary. A similar arrangement may be adopted when, the auxiliary marker laser beam also serving as an alignment beam for the operating laser beam, the superpositioning of the laser beams is to be provided in the resonant cavity of the operating laser generator.

These and other features and advantages of the invention will become apparent from the description which follows, given by way of example, with reference to the accompanying schematic drawings.

BRIEF DESCRIPTION OF THE DRAWINGS

FIG. 1 shows a schematic perspective illustration of an ophthalmic surgical apparatus embodying the invention; and FIG. 2 is a perspective view similar to that of FIG. 1 for an alternative embodiment of the ophthalmic surgical apparatus of the invention.

FIG. 3 is a perspective review illustrating an alternative embodiment of the two successive lenses.

DESCRIPTION OF THE PREFERRED EMBODIMENTS

As shown in the drawings the ophthalmic surgical apparatus embodying the invention generally comprises a laser unit 10 and an operating optical system 11 with the operator's eye schematically shown at 12 and the operating site schematically marked with an "X" at 13.

The laser unit 10 comprises a main laser generator 15 for emitting an operating laser beam of infrared energy, an auxiliary laser generator 16 for emitting a marker beam of visible light and a plurality of reflecting mirrors described in detail hereinbelow for superposing the laser beams at the entrance of the operating optical system 11.

As is known per se, and in particular as disclosed in the European patent publication No. 0007256 the main laser generator 15 comprises a laser head 18 containing a YAG rod doped with neodymium are provided at the respective ends thereof, a cell 19 containing DYE or another saturable absorbent solution and concave mirror, and a Perrot-Fabry interferometer or etalon 20.

In the illustrated embodiment a diaphragm 21 is provided between the laser head 18 and the cell 19.

The axis A1 of the operating laser beam thus defined is successively bent by a reflecting mirror 22 which for reasons which will be better understood below is a dichroic mirror, in other words a mirror which is reflecting for infrared radiation but allows visible light to pass therethrough, a reflecting mirror 23 and a reflecting mirror 24 at the entrance of the operating optical system 11. Mirrors 22, 23 and 24 are all mounted for movement. In practice they are swivelly mounted for movement in all directions.

The auxiliary laser generator 16 is for example a helium-neon laser generator. By means of a reflecting mirror 25 axis A2 of the marker laser beam is directed toward reflecting mirror 23 through partially reflecting mirror 22. Starting from mirror 22 the operating laser beam and the marker laser beam are therefore superposed.

The operating optical system 11 comprises a transfer arm 27 which is formed of successive sections articulated to one another and a slit lamp 28 having a microscope schematically illustrated at 29. The optical system 11 further comprises a focusing lens 30 along its optical path.

The transfer arm 27 is equipped with reflecting mirrors 32. As shown in the embodiments of FIGS. 1 and 2, there is, at least, one reflecting mirror 32 facing reflecting mirror 24 which is the exit mirror from the laser unit 10 and a reflecting mirror 32 at the base of the vertical leg of the slit lamp 28.

Also as illustrated the base of the vertical leg of the slit lamp 28 may also comprise a plurality of reflecting mirrors 34. These arrangements are well known per se and as they are not part of the actual invention, they will not be described in greater detail.

As is also known per se there is associated with each of the laser generators 15 and 16 and beam expander comprising an entrance lens and an exit lens. According to the invention the beam expander for the operating laser beam and the marker laser beam have a common exit lens.

As for the operating laser, the beam expander comprises an entrance leans 36 between the Perrot-Fabry interferometer of etalon 20 and the reflecting mirror 22 and the exit mirror 37 between the reflecting mirrors 23 and 24. In practice, in order to avoid the optical breakdown in the air the entrance lens 36 is a diverging lens; on the other hand the exit lens 37 is a converging lens. The term "lens" is intended to include single lenses as well as a plurality of overlying lenses elements for forming the optical equivalent of a single lens.

Similarly the beam expander for marker laser beam comprises an entrance lens 38 between its laser generator 16 and the reflecting mirror 25 and the exit lens is defined by the exit lens 37 of the beam expander for the operating laser beam. In practice the entrance lens 38 is a converging lens.

As will be noted the common exit lens 37 of the beam expanders 36 and 38 for the operating and marker laser beams have a common section starting from the reflecting mirror 22, and in this common section of the beam expanders the laser beams are superposed before they reach the entrance of the operating optical section 11. Two successive diasporameters 40 are provided along the axis A2 of the marker laser beam between the auxiliary laser generator 16 and the entrance lens 38 of the associated laser beam expander. Thus, the reflecting mirror 25 is advantageously a stationary mirror.

According to the illustrated embodiment of FIG. 3 each of the diasporameters 40 is replaced by a single lens 40' each which induces a prism when the lens is eccentric and each lens 40' is movably mounted in its plane, in a conventional manner i.e., perpendicular to the axis A2 et the corresponding beam.

In any event, as is known per se, the reflecting mirror 24 corrects for any angular error between the laser unit 10 and the operating optical system 11.

If desired, as schematically illustrated in chain-dotted line, the beam of the marker laser 16 may also be used as an alignment laser beam for the beam of the operating laser. To this end it suffices to superpose the beam of the operating laser and the beam of the marker laser 16 inside the resonator of the beam of the operating laser generator. In this case two reflecting mirrors 42 disposed on the other side of the marker laser 16 with respect to the associated beam expander lens 38 and direct the axis A2 of the beam of the marker laser 16 toward the beam of the operating laser the beam of the axis A2 with, as above, passing through two successive diasporameters 43 or two successive lenses which are movably mounted in their respective planes.

In the alternative embodiment illustrated in FIG. 2 the common exit lens of the beam expanders is formed by a focusing lens 30 of the operating optical system 11. In other words the preceding exit lens 37 is eliminated and the focusing lens 30 is constructed and arranged so as to ensure simultaneously the dual function of common exit lens for the beam expanders and focusing lens for the operating optical system 11. In any event as schematically shown at 45 a saturable absorbent solution is preferably provided between the reflecting mirrors 23, 24 of the laser unit 10 to avoid super-radiances.

The various above-mentioned components and their construction are well known to those skilled in the art and therefore will not be described in greater herein.

Obviously the present invention is not intended to be limited to the illustrated and described embodiments but on the contrary includes all alternatives and variations understood to those skilled in the art without departing from the spirit and scope of the invention.

What is claimed is:

1. An ophthalmic surgical apparatus comprising a main laser genrator for emitting an operating laser beam of infrared energy and an auxiliary marker laser for emitting a marker laser beam of visible light, means for superposing the laser beams of the operating laser and the auxiliary marker laser before reaching an operating optical system, said means for superposing the laser beams of the operating laser and the auxiliary marker laser including a plurality of mirrors and a laser beam expander for expanding each of the laser beams, said laser beam expanders each having separate entrance lenses and sharing a common exit lens.

2. The surgical apparatus of claim 1, wherein said operating optical system comprises a focusing lens, said focusing lens defining said common exit lens of said laser beam expanders.

3. The surgical apparatus of claim 2, wherein said entrance lens of said operating laser beam expander is a diverging lens.

4. The surgical apparatus of claim 2, wherein said means for superposing said laser beams further comprises two successive diasporameters disposed along said marker laser beam and between said auxiliary marker laser and said entrance lens of said marker laser beam expander.

5. The surgical apparatus of claim 2, wherein said means for superposing said laser beams further comprises two successive lenses movably mounted in their respective planes, and disposed along said marker laser beam and between said auxiliary marker laser and said entrance lens of said marker laser beam expander.

6. The surgical apparatus of claim 2, wherein said means for superposing said laser beams further comprises two successive diasporameters disposed along said marker beam between said auxiliary marker laser and said operating laser, whereby said marker laser beam is superposed on said operating laser beam inside said operating laser.

7. The surgical apparatus of claim 6, wherein said operating laser comprises a laser head, a cell on one side and an interferometer on the other side of said laser head, said diasporameters being disposed between said auxiliary marker laser and said cell of said operating laser.

8. The surgical apparatus of claim 1 wherein said entrance lens of said operating laser beam expander is a diverging leans.

9. The surgical apparatus of claim 1, wherein said means for superposing said laser beams further comprises two successive diasporameters disposed along said marker laser beam between said auxiliary marker laser and said entrance lens of said marker laser beam expander.

10. The surgical apparatus of claim 1, wherein said means for superposing said laser beams further comprises two successive lenses movably mounted in their respective planes, and disposed along said marker laser beam and between said auxiliary marker laser and said entrance lens of said marker laser beam expander.

11. The surgical apparatus of claim 1, wherein said means for superposing said laser beams further comprises two successive diasporameters disposed along said marker laser beam between said auxiliary marker laser and said operating laser, whereby said marker laser beam is superposed on said operating laser beam inside said operating laser.

12. The surgical apparatus of claim 11, wherein said operating laser comprises a laser head, a cell on one side and an interferometer on the other side of said laser head, said diasporameters being disposed between said auxiliary marker laser and said cell of said operating laser.

* * * * *